(12) United States Patent
He et al.

(10) Patent No.: US 7,960,181 B2
(45) Date of Patent: Jun. 14, 2011

(54) CHROMOIONOPHORE AND METHOD OF DETERMINING POTASSIUM IONS

(75) Inventors: Huarui He, Alpharetta, GA (US); Chao Lin, Alpharetta, GA (US); Neeta Raje, Alpharetta, GA (US); Chuseng Liu, Atlanta, GA (US)

(73) Assignee: OPTI Medical Systems, Westbrook, ME (US)

( * ) Notice: Subject to any disclaimer, the term of this patent is extended or adjusted under 35 U.S.C. 154(b) by 903 days.

(21) Appl. No.: 11/743,569

(22) Filed: May 2, 2007

(65) Prior Publication Data

US 2007/0259443 A1   Nov. 8, 2007

Related U.S. Application Data

(60) Provisional application No. 60/796,934, filed on May 3, 2006.

(51) Int. Cl.
  *C07D 245/00* (2006.01)
  *C07D 245/04* (2006.01)
  *C07D 245/06* (2006.01)
  *C07D 487/00* (2006.01)

(52) U.S. Cl. .................... 436/166; 540/470; 540/471

(58) Field of Classification Search .......... None
See application file for complete search history.

(56) References Cited

U.S. PATENT DOCUMENTS

| | | | |
|---|---|---|---|
| 4,367,072 A | 1/1983 | Vögtle et al. |
| 4,994,395 A | 2/1991 | Chapoteau et al. |
| 5,011,924 A | 4/1991 | Cram et al. |
| 6,211,359 B1 | 4/2001 | He et al. |

OTHER PUBLICATIONS

Sax and Lewis. Hawley's Condensed Chemical Dictionary, 1987, pp. 281-282, "chromophore" entry.*
Ingle and Crouch, Spectrochemical Analysis, 1988, p. 2, table 1-1.*
Padmawar et al. Nature Methods, 2005, 2(11), 825-27.*
Helgeson et al., "Host-Guest Complexation. 50. Potassium and Sodium Ion-Selective Chromogenic Ionophores" J. Am Chem. Soc., vol. 111. 1989, 6339-6350.
Burtis et al., ed. "Tietz Textbook of Clinical Chemistry and Molecular Diagnostics" Elsevier Sauders, St. Louis, MO, USA 2006, p. 986-989.
He et al., "A Fluorescent Chemosensor for Sodium Based on Photoinduced Electron Transfer" Anal. Chem.. vol. 75, 2003 449-555.
He, et al., "A Fluorescent Sensor with High Selectivity and Sensitivity for Potassium in Water" J. Am. Chem. Soc. vol. 125, 2003, 1468-1469.

* cited by examiner

*Primary Examiner* — James O Wilson
*Assistant Examiner* — Noble Jarrell
(74) *Attorney, Agent, or Firm* — Gilberto M. Villacorta; Steven M. Reid; Foley & Lardner LLP

(57) ABSTRACT

The invention relates to methods of determining potassium ions in a sample, wherein the ions are contacted with a compound having chromophoric moiety and an ionophoric moiety, where the ionophoric moiety interacts with the potassium ions present in the sample, resulting in the chromophoric moiety changing its radiation absorption properties in the ultraviolet and visible regions of the spectrum. For example, a change in an intensity of an absorption maximum is measured and the ion concentration is determined accordingly.

17 Claims, 3 Drawing Sheets

$R^{12}$ = hydrogen, -NO$_2$, -NO, -CN, C$_1$-C$_8$ straight chain or branched alkyl, (C$_2$-C$_8$)alkenyl, halogen, -SO$_3$H, -Q-COOH, -Q-N(R$^{14}$)$_3$, -C(O)OR$^{14}$, -C(O)R$^{14}$

CHROMOIONOPHORE AND METHOD OF DETERMINING POTASSIUM IONS

BACKGROUND OF THE INVENTION

The invention relates to a chromoionophore comprising an chromophore and an ionophore capable of selectively binding potassium ions for determining potassium ion in a sample. The present invention also relates to a method of determining the concentration of potassium ions in a sample wherein the chromoionophore is contacted with potassium ion in a sample, wherein the intensity of at least one absorption maximum in the visible region changes and the concentration of potassium ion is calculated based on the change in the intensity of the absorption maximum.

The accurate measurement of physiologic cations, such as sodium, potassium, lithium, calcium, and magnesium, is essential in clinical diagnosis. Traditionally, these ions were determined in plasma or serum using ion-selective electrodes (ISE), which are very cumbersome to use and costly to maintain. Serious drawbacks of electrochemical measuring arrangements are the requirement of a reference element, sensitivity towards electrical potentials and electromagnetic interference.

U.S. Pat. No. 4,367,072 describes a process for the determination of metal ions using simple crown ethers as ion-binding units. However, the binding is too weak to be useful for many practical applications, such as clinical applications, in which the indicator has to discriminate between ions with very similar properties, e.g., sodium versus potassium or magnesium versus calcium.

U.S. Pat. No. 5,011,924 and U.S. Pat. No. 4,994,395 describe cryptands (or cryptohemispherands) linked with an ionizable chromophore, which changes its color upon binding of ions based on charge interaction between the bound cation and the anion of chromophore. Although all nitrogen atoms in these cryptands are aliphatic, and not electronically conjugated with the chromophore, the results of measurement of serum samples using these chromoionophores are impressive and promising (Helgeson et. al. *J. Am. Chem. Soc.*, vol. 111, 1989, 6339-6350). However, the syntheses of these cryptands, especially of those cryptohemispherands, are lengthy and tedious. Consequently, the manufacturing cost of these reagents remains prohibitively high even in the decades following their discovery. The cost factor could be a reason why these reagents have not replaced those ISE modules in most large clinical analyzers, in which the ISE methods are still dominating (see Burtis et. al. ed. "Tietz Textbook of Clinical chemistry and Molecular Diagnostics" Elsevier Sauders, St. Louis, Mo., USA 2006, page 986).

U.S. Pat. No. 6,211,359 (which is hereby incorporated by reference in its entirety) reports ionophores for potassium, which have π-electron conjugated nitrogen and were coupled to a fluorophore to make luminophore-ionophore sensors where the respective ions are detected by measuring luminescence emission. This ionophore has been proven to be very selective in determination of potassium in whole blood (see He et. al. *Anal. Chem. Vol.* 75, 2003, 449-555; and *J. Am. Chem. Soc. vol.* 125, 2003, 1468-1469), thus showing that the ionophores are effective at physiological pH.

By coupling to a chromophoric moiety, these ionophores can be converted into colorimetric sensors. The chromophoric moieties can be a nitro-substituted styryl or phenylazo, substituted thiazolevinyl or thiazoleazo, substituted naphthothiazolevinyl or naphthothiazoleazo, substituted naphthylvinyl or naphthylazo, substituted quinolinovinyl or quinolinoazo and their quarternized salts. To date, there has been no systematic investigation of these types of colorimetric reagents. The water solubility of the reagents can be improved dramatically if a charge is introduced into the dye molecules. The absorption wavelength can be red-shifted by replacing the nitrophenyl with a nitrothiazole or larger chromophore-generating substituent.

The present invention provides chromoionophores that are water soluble and can be reliably used for detection of ions in samples that absorb at wavelengths longer than about 400 nm. Examples of such samples are biological fluids.

For the chromoionophores of the present invention, the amount of ion present is determined by measuring changes in the intensity of at least one absorption maximum of the chromoionophore upon contacting the chromoionophore with an ion. The measurements are done by using standard centralized instruments, such as ultraviolet-visible spectrometers. A calibration curve for an ion is generated from a series of empirically determined absorption spectra. A calibration curve is useful for at-once determining the concentration of ion in a sample from the measured absorbance.

The chromoionophores of this invention absorb visible light (about 400 nm or greater) with reasonable extinction coefficient, thus avoiding those practical problems associated with variable background absorption from optical components, cuvette polymer materials, and biological samples. Further, the invention is well suited for practice in the determination of potassium ion in the presence of physiological concentrations of other alkali ions.

SUMMARY OF THE INVENTION

The present invention relates to novel chromoionophores, comprising a chromophoric moiety and an ionophoric moiety. The invention further relates to a method of determining potassium ions in a sample, wherein the ions are contacted with the chromoionophore, where the ionophoric moiety interacts with the potassium ions present in the sample, resulting in the chromophoric moiety changing its radiation absorption properties in the ultraviolet and visible regions of the spectrum. In one embodiment, a change in an intensity of an absorption maximum is measured and the ion concentration is determined accordingly.

In one embodiment, the chromoionophores of the invention comprise an ionophore having one or more chelating moieties that is capable of selectively binding potassium ions and a chromophore having a plurality of conjugated unsaturated bonds. The chromoionophore exhibits at least one absorption maximum having a wavelength in the visible region having a first intensity such that the absorption maximum obtains a second intensity that is different from the first intensity by an amount that is proportional to the concentration of potassium ion present in a mixture comprising potassium ions and the chromoionophore.

In other embodiments, the chromoionophores of the invention are compounds having the Formula (I)

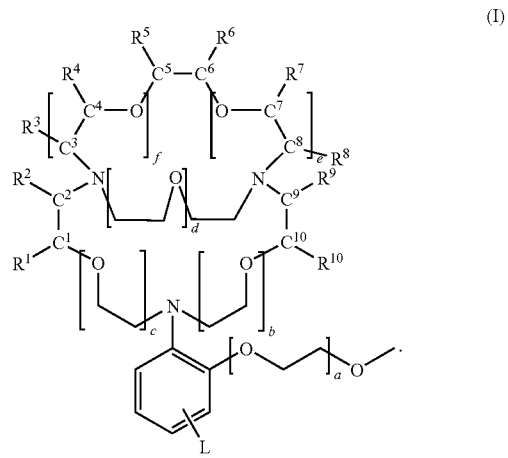

(I)

wherein a is 0 or 1, and b and c independently are selected from the group consisting of 0 and 1. It should be understood that b and c are not simultaneously 0.

Variable d is selected from the group consisting of 1, 2 and 3. Variables e and f independently are selected from the group consisting of 0 and 1. It should be understood that e and f are not simultaneously 0.

Each of $R^1$ and $R^2$ is hydrogen or $R^1$ and $R^2$, together with $C^1$ and $C^2$, form a ($C_1$-$C_4$) alkyl benzene ring or a ($C_1$-$C_4$) alkoxy benzene ring.

Each of $R^3$ and $R^4$ is hydrogen or $R^3$ and $R^4$, together with $C^3$ and $C^4$, form a ($C_1$-$C_4$) alkyl benzene ring or a ($C_1$-$C_4$) alkoxy benzene ring.

Each of $R^5$ and $R^6$ is hydrogen or $R^5$ and $R^6$, together with $C^5$ and $C^6$, form a benzene ring or a naphthalene ring.

Each of $R^7$ and $R^8$ is hydrogen or $R^7$ and $R^8$, together with $C^7$ and $C^8$, form a ($C_1$-$C_4$) alkyl benzene ring or a ($C_1$-$C_4$) alkoxy benzene ring.

Each of $R^9$ and $R^{10}$ is hydrogen or $R^9$ and $R^{10}$, together with $C^9$ and $C^{10}$, form a ($C_1$-$C_4$) alkyl benzene ring or a ($C_1$-$C_4$) alkoxy benzene ring.

L is a chromophoric moiety.

The invention further provides a method of determining the concentration of potassium ions in a sample comprising (a) measuring the intensity of at least one absorption maximum of a solution of a chromoionophore sensitive to the presence of potassium ions in solution to obtain a first intensity; wherein the concentration of the chromoionophore in solution is known; and wherein said at least one absorption maximum has a wavelength in the visible region;

(b) contacting the solution of the chromoionophore with the sample; whereby the first intensity changes;

(c) measuring the intensity of at least one absorption maximum to obtain a second intensity;

(d) deriving the concentration of potassium ion in the sample based, in part, on the difference between the first and second intensities.

In one embodiment, at least one absorption maximum occurs at a wavelength that is in the visible region.

In another embodiment, the difference between the first and second intensities results in a calorimetric change in the solution sample comprising the chromoionophore and potassium ions.

In another embodiment, at least one absorption maximum occurs at a wavelength of about 400 nm or greater.

In another embodiment, at least one absorption maximum occurs at a wavelength between about 400 nm and about 800 nm.

DETAILED DESCRIPTION OF THE INVENTION

Figure 1:
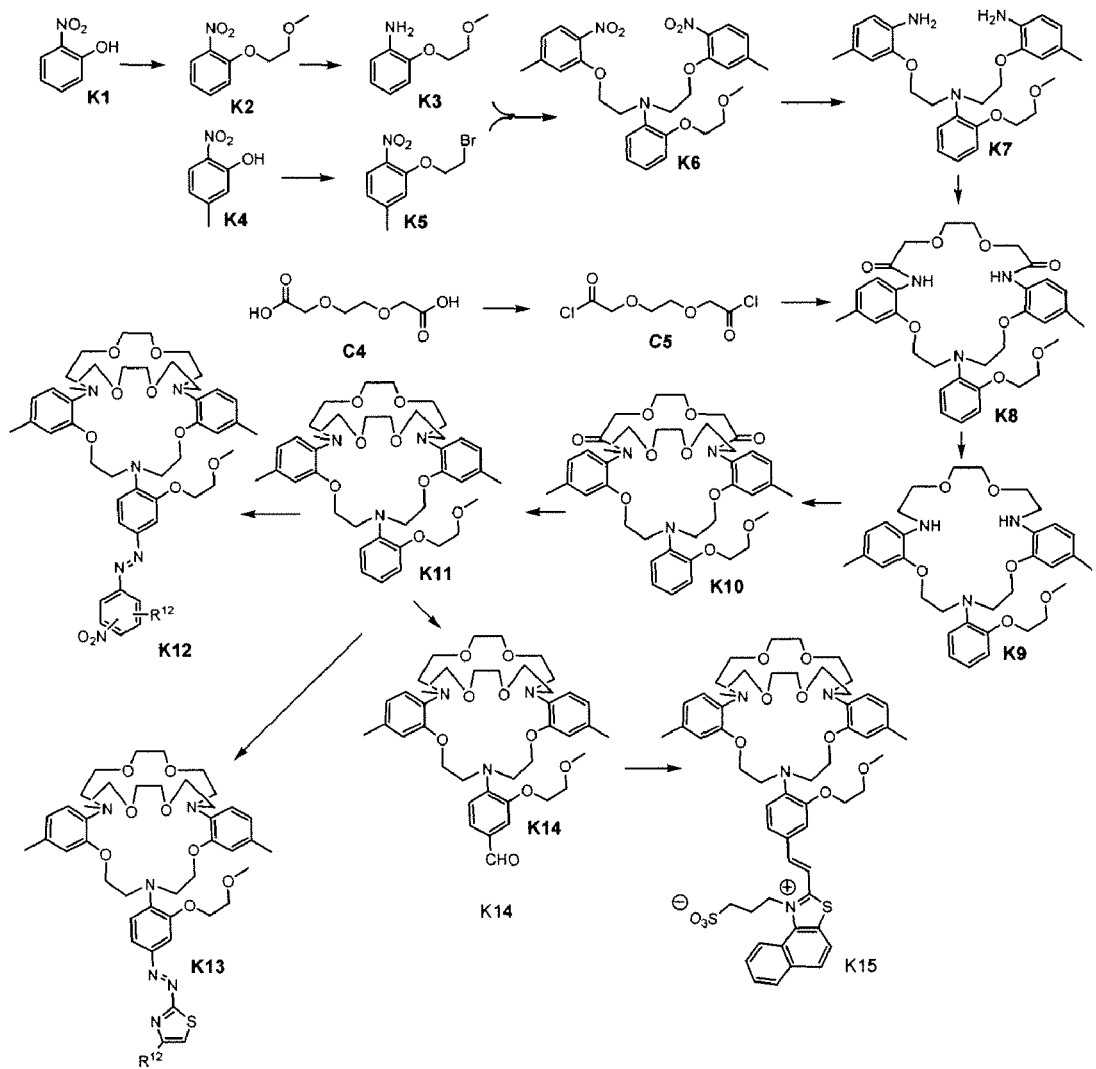
FIG. 1 is an illustration of a synthetic pathway for a potassium calorimetric indicator.

As used herein, the terms have the following meanings:

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents.

The term "alkylene" refers to a divalent alkyl group (e.g., an alkyl group attached to two other moieties, typically as a linking group). Examples of a ($C_1$-$C_7$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. An alkylene group can be unsubstituted or optionally substituted with one or more substituents.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents.

The term "Ar" as used herein refers to an aromatic or heteroaromatic moiety. An "aromatic" moiety refers to a 6- to 14-membered monocyclic, bicyclic or tricyclic aromatic hydrocarbon ring system. Examples of an aromatic group include phenyl and naphthyl. An aromatic group can be unsubstituted or optionally substituted with one or more substituents. The term "heteroaromatic" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaromatics are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, naphthothiazolyl, quinoxalinyl. A heteroaromatic group can be unsubstituted or optionally substituted with one or more substituents.

The term "halogen" as used herein refers to —F, —Cl, —Br or —I.

As used herein, the term "heteroatom" is meant to include oxygen (O), nitrogen (N), and sulfur (S).

The term "chromoionophore" as used herein refers to a compound comprising at least one ionophore and at least one chromophore.

The following abbreviations are used herein and have the indicated definitions: LAH is lithium aluminum hydride; DMF is dimethylformamide; NMR is nuclear magnetic resonance; THF is tetrahydrofuran.

Compounds of the Invention

The present invention provides compounds of Formula (I) referred to as "chromoionophores"

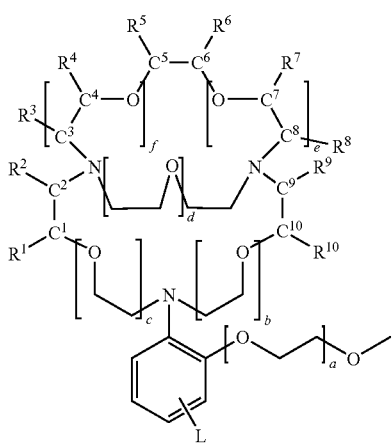

wherein a, b, c, d, e, f, $R^1$, $R^2$, $R^3$, $R^4$, $R^5$, $R^6$, $R^7$, $R^8$, $R^9$, and $R^{10}$ are as defined above.

In one embodiment, the chromophoric moiety L is selected from the group consisting of $NO_2$, Formula (II) and (III),

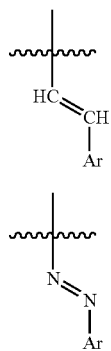

(II)

(III)

wherein, Ar is a $(C_6\text{-}C_{10})$ aromatic moiety or a $(C_5\text{-}C_{14})$ heteroaromatic moiety containing one or more heteroatoms selected from N, O, and S, and wherein Ar is substituted with one or more substituents selected from the group consisting of hydrogen, $-NO_2$, $-NO$, $-CN$, $(C_1\text{-}C_8)$ straight chain or branched alkyl, $(C_2\text{-}C_8)$ alkenyl, halogen, $-SO_3H$, $-W-COOH$, $-W-N(R^{11})_3$, $-C(O)OR^{11}$, $-C(O)R^{11}$; W is $(C_1\text{-}C_8)$ alkylene; and $R^{11}$ is selected from the group consisting of hydrogen and $(C_1\text{-}C_8)$ straight chain or branched alkyl.

In another embodiment, Ar is selected from the group consisting of Formula (IV), (V), (VI), and (VII)

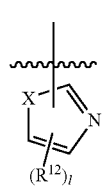

(IV)

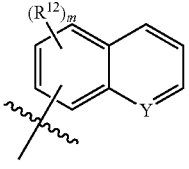

(V)

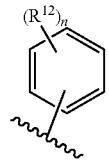

(VI)

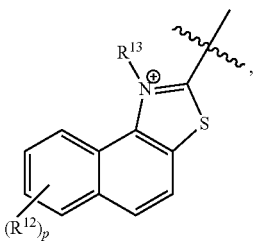

(VII)

wherein X is O or S, and Y is N or C.

$R^{12}$, at each occurrence, is independently selected from the group consisting of hydrogen, $-NO_2$, $-NO$, $-CN$, $C_1\text{-}C_8$ straight chain or branched alkyl, $(C_2\text{-}C_8)$ alkenyl, halogen, $-SO_3H$, $-Q\text{-}COOH$, $-Q\text{-}N(R^{14})_3$, $-C(O)OR^{14}$, $-C(O)R^{14}$.

$R^{13}$ is $-Q\text{-}SO_3^-$ or $-Q\text{-}COO^-$.

Q is $(C_1\text{-}C_8)$ alkylene.

$R^{14}$ is selected from the group consisting of hydrogen and $(C_1\text{-}C_8)$ straight chain or branched alkyl.

Variable l is an integer selected from 1 to 3; m is an integer selected from 1 to 7; n is an integer selected from 1 to 5; and p is an integer selected from 1 to 6.

In yet another embodiment, a=1, b=1, c=1, d=1, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, taken together with $C^9$ and $C^{10}$, form a toluene ring.

In another embodiment, a=1, b=1, c=1, d=1, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.

In another embodiment, a=1, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, together with $C^9$ and $C^{10}$, form a toluene ring.

In another embodiment, a=1, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.

In one embodiment, a=0, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, together with $C^9$ and $C^{10}$, form a toluene ring.

In one embodiment, a=0, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.
Specific examples of compounds of Formula (I) are provided below:
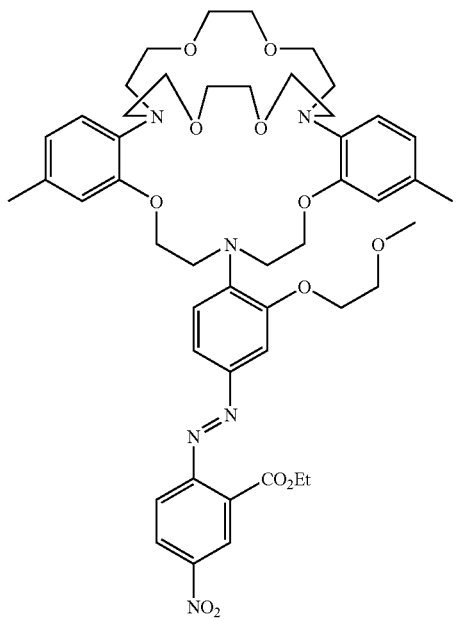
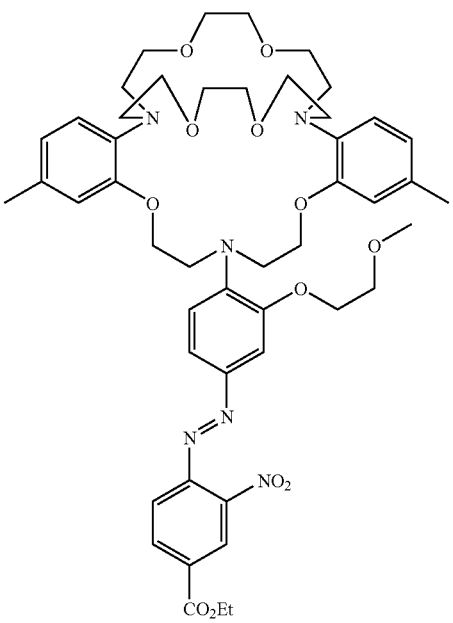
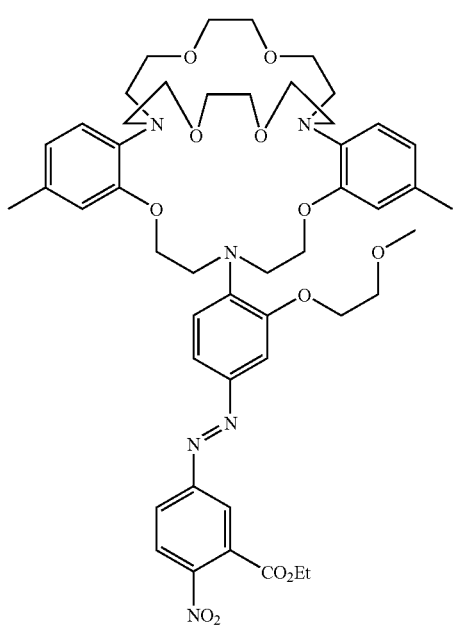
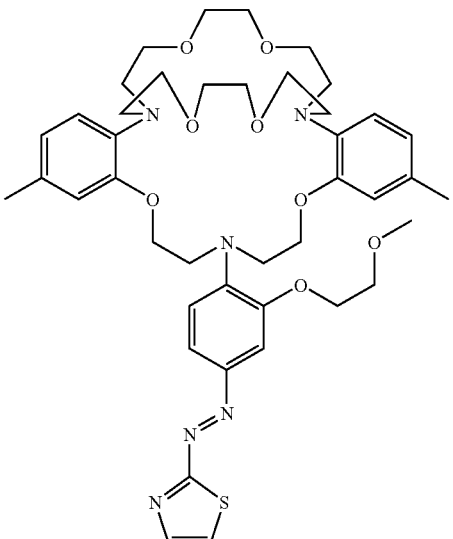

9
-continued

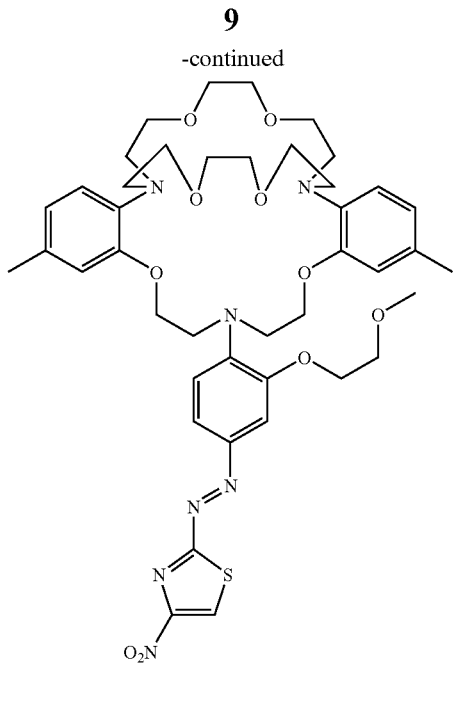

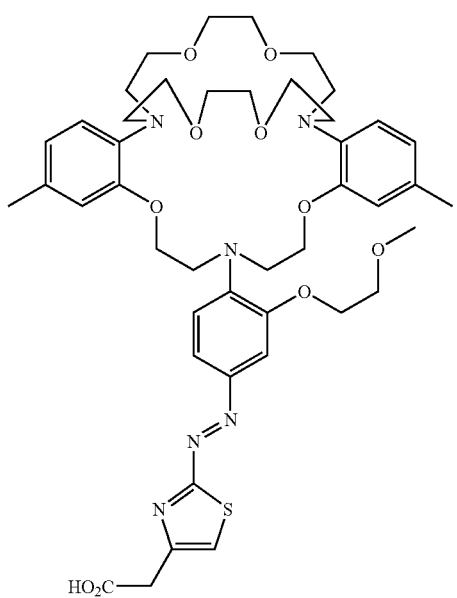

10
-continued

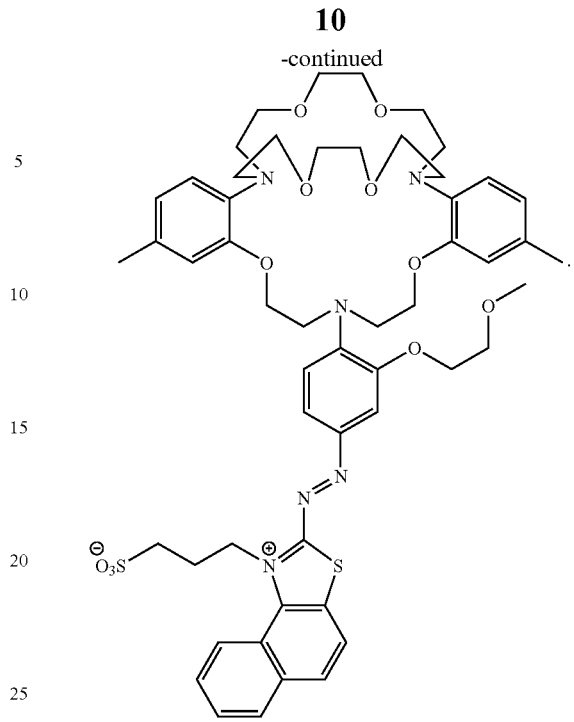

In one embodiment, the invention provides for a method of determining potassium ions in a sample comprising a chromoionophore and potassium ions, where the chromoionophore is a compound of the general Formula (I)

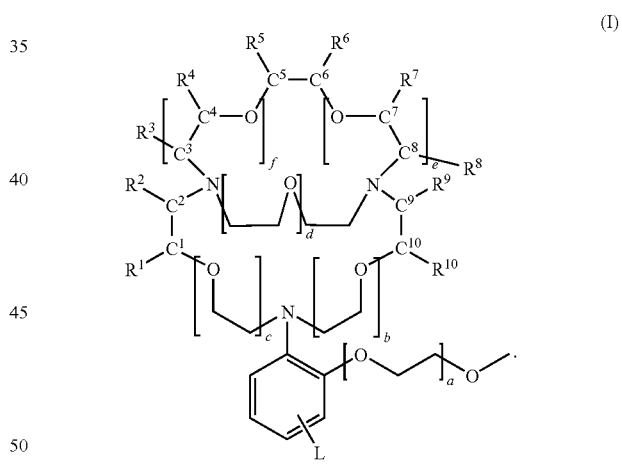

(I)

wherein a is 0 or 1, and b and c independently are selected from the group consisting of 0 and 1. It should be understood that b and c are not simultaneously 0.

Variable d is selected from the group consisting of 1, 2 and 3. Variables e and f independently are selected from the group consisting of 0 and 1. It should be understood that e and f are not simultaneously 0.

Each of $R^1$ and $R^2$ is hydrogen or $R^1$ and $R^2$, together with $C^1$ and $C^2$, form a ($C_1$-$C_4$) alkyl benzene ring or a ($C_1$-$C_4$) alkoxy benzene ring.

Each of $R^3$ and $R^4$ is hydrogen or $R^3$ and $R^4$, together with $C^3$ and $C^4$, form a ($C_1$-$C_4$) alkyl benzene ring or a ($C_1$-$C_4$) alkoxy benzene ring.

Each of $R^5$ and $R^6$ is hydrogen or $R^5$ and $R^6$, together with $C^5$ and $C^6$, form a benzene ring or a naphthalene ring.

Each of $R^7$ and $R^8$ is hydrogen or $R^7$ and $R^8$, together with $C^7$ and $C^8$, form a $(C_1-C_4)$ alkyl benzene ring or a $(C_1-C_4)$ alkoxy benzene ring.

Each of $R^9$ and $R^{10}$ is hydrogen or $R^9$ and $R^{10}$, together with $C^9$ and $C^{10}$, form a $(C_1-C_4)$ alkyl benzene ring or a $(C_1-C_4)$ alkoxy benzene ring L is a chromophoric moiety.

The invention further provides methods of determining potassium ion in a sample comprising a chromoionophore according to Formula (I) and potassium ions, where the chromophoric moiety L is selected from the group consisting of Formula (II) and (III),

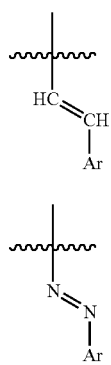

(II)

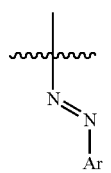

(III)

wherein, Ar is a $(C_6-C_{10})$ aromatic moiety or a $(C_5-C_{14})$ heteroaromatic moiety containing one or more heteroatoms selected from N, O, and S, and wherein Ar is substituted with one or more substituents selected from the group consisting of hydrogen, —$NO_2$, —NO, —CN, $(C_1-C_8)$ straight chain or branched alkyl, $(C_2-C_8)$ alkenyl, halogen, —$SO_3H$, —W—COOH, —W—$N(R^{11})_3$, —$C(O)OR^{11}$, —$C(O)R^{11}$; W is $(C_1-C_8)$ alkylene; and $R^{11}$ is selected from the group consisting of hydrogen and $(C_1-C_8)$ straight chain or branched alkyl.

The invention further provides methods of determining potassium ion in a sample comprising a chromoionophore according to Formula (I) and potassium ions, where Ar is selected from the group consisting of Formula (IV), (V), (VI), and (VII)

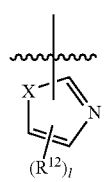

(IV)

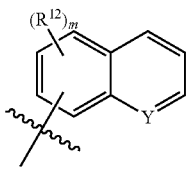

(V)

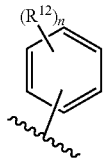

(VI)

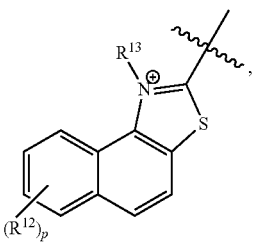

(VII)

wherein X is O or S, and Y is N or C.

$R^{12}$, at each occurrence, is independently selected from the group consisting of hydrogen, —$NO_2$, —NO, —CN, $C_1-C_8$ straight chain or branched alkyl, $(C_2-C_8)$ alkenyl, halogen, —$SO_3H$, -Q-COOH, -Q-$N(R^{14})_3$, —$C(O)OR^{14}$, —$C(O)R^{14}$.

$R^{13}$ is -Q-$SO_3^-$ or -Q-$COO^-$.

Q is $(C_1-C_8)$ alkylene.

$R^{14}$ is selected from the group consisting of hydrogen and $(C_1-C_8)$ straight chain or branched alkyl.

Variable l is an integer selected from 1 to 3; m is an integer selected from 1 to 7; n is an integer selected from 1 to 5; and p is an integer selected from 1 to 6.

The invention further provides methods of determining potassium ion in a sample comprising a chromoionophore according to Formula (I) and potassium ions, where a=1, b=1, c=1, d=1, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, together with $C^9$ and $C^{10}$, form a toluene ring.

The invention further provides methods of determining potassium ion in a sample comprising a chromoionophore according to Formula (I) and potassium ions, where a=1, b=1, c=1, d=1, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.

The invention further provides methods of determining potassium ion in a sample comprising a chromoionophore according to Formula (I) and potassium ions, where a=1, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, together with $C^9$ and $C^{10}$, form a toluene ring.

The invention further provides methods of determining potassium ion in a sample comprising a chromoionophore according to Formula (I) and potassium ions, where a=1, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.

The invention further provides methods of determining potassium ion in a sample comprising a chromoionophore according to Formula (I) and potassium ions, where a=0, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring; $R^9$ and $R^{10}$, together with $C^9$ and $C^{10}$, form a toluene ring.

The invention further provides methods of determining potassium ion in a sample comprising a chromoionophore according to Formula (I) and potassium ions, where a=0, b=1, c=1, d=2, e=1, f=1; each of $R^3$, $R^4$, $R^5$, $R^6$, $R^7$, and $R^8$ is hydrogen; $R^1$ and $R^2$, together with $C^1$ and $C^2$, form a toluene ring, wherein $C^2$ is in the para position relative to the amine on the ring; $R^9$ and $R^{10}$, together with $C^9$ and $C^{10}$, form a toluene ring, wherein $C^9$ is in the para position relative to the amine on the ring.

The invention further provides methods of determining potassium ion in a sample comprising a chromoionophore according to Formula (I) and potassium ions, where the sample is a biological fluid. Examples of biological fluids are whole blood, plasma, serum, and urine.

The invention further provides methods of determining potassium ion in a sample comprising a chromoionophore according to Formula (I) and potassium ions, where the sample has a pH of 6.5 or above.

Preparation of the Compounds of Formula (I)

Those skilled in the art will recognize that there are a variety of methods available to synthesize molecules described herein. The general strategy for syntheses of colorimetric triazacryptand is to synthesize triazacryptand, which is then coupled with a visible color-generating electrophile, such as a nitrophenyldiazonium salt (FIG. 1). Triazacryptands can be prepared according to the following procedure: para-Methylnitrophenol (K4) is alkylated with large excess of dibromoethane to give bromoethoxymethyl-nitrophenylether (K5), which is used to dialkylate dinitrophenoxy-alkyl-aniline (K3). The dinitro compound (K6) is hydrogenated to afford diamine (K7), which is acylated with diacid chloride (C5) under high dilution conditions to obtain the cyclic diamide (K8). The diamide can be reduced to triazacrown ether (K9) with borane or LAH in THF. It is recommended that borane should be used to reduce aromatic diamide. The triazacrown ether (K9) is reacted with diacid chloride (C5) again to give tertiary amide (K10). The amide can be reduced with borane in THF to afford the ionophore (K11). This ionophore can be coupled with diazonium salts to get final colorimetric potassium indicators (K12).

Example 1

Synthesis of K5. 122.5 g (800 mmol) 5-methyl-2-nitrophenol (K4), 751.0 g (4000 mmol) 1,2-dibromoethane, 110.7 g (800 mmol) $K_2CO_3$ were suspended in 400 mL anhydrous DMF. Heated at 120° C. for 1 hour, cooled, and most of the liquid was evaporated. The residue was dissolved in 1 L $CHCl_3$ and 1 L water. The organic layer washed with 2×1 1.8% NaOH until the aqueous layer became pale yellow. The organic layer was dried over $Na_2SO_4$. Filtered and the solvent was evaporated to give ~240 g oil. The oil was triturated with 240 mL boiling methanol and allowed to sit for 2 hours. The resulting precipitate was filtered and washed with 2×100 mL cold methanol, dried at room temperature for 18 h to afford 103.4 g off-white crystal with a melting point 45-47° C. $H^1$NMR (300 MHz, $CDCl_3$) δ (ppm): 2.40 (s, 3H, Ar—$CH_3$), 3.65 (t, 2H, $CH_2Br$), 4.30 (t, 2H, $ArOCH_2$), 6.85-7.75 (m, 3H, Ar—H). Anal. Calcd for $C_9H_{10}BrNO_3$: C, 41.56; H, 3.88; N, 5.39. Found: C, 41.96; H, 3.92; N, 5.53.

Example 2

Synthesis of K2. A suspension of 140 g (1010 mmol) 2-nitrophenol (K1), 105 g (1110 mmol) chloroethyl methyl ether, 84.2 g (507 mmol) KI, 153 g (1110 mmol) $K_2CO_3$ and 500 mL DMF was heated at 110±5° C. for 6 h. Solvent was evaporated and the residue was dissolved in 500 mL $CHCl_3$ and 500 mL water. Organic phase washed with 2×500 mL 2.5% $Na_2CO_3$, 500 mL sat. NaCl, dried over $Na_2SO_4$. The solvent was evaporated to afford 161 g light yellow oil. $H^1$NMR (300 MHz, $CDCl_3$) δ (ppm) 3.45 (s, 3H, $OCH_3$), 3.78 (t, 2H, $OCH_2$), 4.25 (t, 2H, $ArOCH_2$), 7.02-7.82 (m, 4H, Ar—H). Anal. Calcd for $C_9H_{11}NO_4$: C, 54.82; H, 5.62; N, 7.10. Found: C, 54.63; H, 5.82; N, 7.43.

Example 3

Synthesis of K3. 60.5 g (30.7 mmol) K2 was dissolved in 200 mL methanol, 3.0 g 10% palladium on activated carbon was added. This suspension was hydrogenated at 2.2 atm. for 18 h, until no more hydrogen uptake was observed. The catalyst was filtered off and the solvent was evaporated to afford 48.7 g light yellow oil. $H^1$NMR (300 MHz, $CDCl_3$) δ (ppm) 3.45 (s, 3H, $OCH_3$), 3.65 (br. s, 2H, Ar—$NH_2$), 3.78 (t, 2H, $OCH_2$), 4.20 (t, 2H, $ArOCH_2$), 6.74-6.82 (m, 4H, Ar—H). Anal. Calcd for $C_9H_{13}NO_2$: C, 64.65; H, 7.84; N, 8.38. Found: C, 64.27; H, 8.08; N, 8.58.

Example 4

Synthesis of K6. A suspension of 16.7 g (100 mmol) K3, 78.0 g (300 mmol) K5, 41.4 g (300 mmol) $K_2CO_3$ and 24.9 g (150 mmol) KI in 200 mL acetonitrile was heated under reflux for 20 h. Then 26 g (100 mmol) product from step (a), 13.8 g (100 mmol) $K_2CO_3$ were added. Continued to heat for another 20 h. Then 26 g (100 mmol) product from step (a), 13.8 g (100 mmol) $K_2CO_3$ were added again. Continued to heat for 20 h. The mixture was cooled and solvent was evaporated. The residue was dissolved in 500 mL $CHCl_3$ and 500 mL saturated NaCl, dried over $Na_2SO_4$. Solvent was evaporated to give 120 g oil. This oil was triturated with 120 mL boiling methanol, hot filtered. Dried at RT for 18 h. afforded 30.4 g bright yellow crystal. This crystal was recrystallized from about 2 L ethanol, afforded 29.0 g bright yellow crystal with a melting point 120-123° C. $H_1$NMR (300 MHz, $CDCl_3$) δ (ppm) 2.35 (s, 6H, Ar—$CH_3$), 3.35 (s, 3H, $OCH_3$), 3.70 (t, 2H, $OCH_2$), 3.75 (t, 4H, $NCH_2$), 4.10 (t, 2H, $ArOCH_2$), 4.20 (t, 4H, $O_2N$—$ArOCH_2$), 6.85-7.75 (m, 10H, Ar—H). Anal. Calcd for $C_{27}H_{31}N_3O_8$: C, 61.70; H, 5.95; N, 8.00. Found: C, 61.33; H, 6.03; N, 7.98.

Example 5

Synthesis of K7. 54.0 g (100 mmol) K6 was dissolved in 500 mL DMF, 2.7 g 10% palladium on activated carbon was added. This suspension was hydrogenated at 2.2 atm. for 18 h, till no more hydrogen uptake was observed. The catalyst was filtered off and the solvent was evaporated. The residue was dried in a vacuum desiccator over $P_2O_5$ for 24 h at room temperature, affording 46.8 g (97%) light brown oil. $H^1$NMR (300 MHz, $CDCl_3$) δ (ppm) 2.20 (s, 6H, Ar—$CH_3$), 3.35 (s, 3H, $OCH_3$), 3.45 (br.s, 4H, Ar—$NH_2$), 3.70 (m, 6H, 2×$NCH_2$ and $CH_2OCH_3$), 4.10 (m, 6H, $ArOCH_2$), 6.60-7.10 (m, 10H, Ar—H). Anal. Calcd for $C_{27}H_{35}N_3O_4$: C, 69.65; H, 7.58; N, 9.03. Found: C, 69.03; H, 7.68; N, 9.18.

Example 6

Synthesis of C5. 125 g (702 mmol) 3,6-dioxa-1,8-octanedioic acid (C4) was suspended in 800 mL anhydrous benzene. 250 g (1970 mmol) oxalyl chloride and 20 drops of pyridine were added, then stirred at RT for 16 h. Solvent was evaporated at 40° C. and residue was re-dissolved in 2×800 mL benzene and evaporated off. Pump oil was applied to reduce the pressure down to ~5 mmHg to remove oxalyl chloride completely. Afforded 148 g light yellow oil. $H^1$NMR (CDCl$_3$) δ (ppm) 3.76 (s, 4H), 4.45 (s, 4H).

Example 7

Synthesis of K8. 46.8 g (100.6 mmol) K7 and 22.4 g (221.3 mmol) triethylamine were dissolved in 500 mL anhydrous CH$_2$Cl$_2$ in a 500 mL additional funnel, while 23.8 g (110.6 mmol) (C5) was dissolved in 500 mL CH$_2$Cl$_2$ in another 500 mL additional funnel. The solutions in two additional funnels were added slowly into a 5 l flask containing 2.5 l anhydrous CH$_2$Cl$_2$ during 8 h. Stirred at room temperature for 20 h. The solution washed with 2×2.5 l 0.2 N HCl and dried over Na$_2$SO$_4$. Solvent was evaporated to give 60 g white solid. The solid was triturated with 200 mL hot methanol, filtered, washed the solid with 2×100 mL methanol, dried at RT for 18 h. gave 55 g crude product. This crude product was purified with 240 g silica gel 60 using CHCl$_3$ and CHCl$_3$/MeOH (97/3, v/v) as eluent, afforded 41.91 g white powder. $H^1$NMR (300 MHz, CDCl$_3$) δ (ppm) 2.25 (s, 6H, Ar—CH$_3$), 3.45 (s, 3H, OCH$_3$), 3.75-4.15 (m, 20H, OCH$_2$ and NCH$_2$), 6.50-8.20 (m, 10H, Ar—H), 9.10 (s. 2H, C(O)N—H). Anal. Calcd for C$_{33}$H$_{41}$N$_3$O$_8$: C, 65.22; H, 6.80; N, 6.91. Found: C, 64.18; H, 6.89; N, 6.82.

Example 8

Synthesis of K9. A solution of 35.0 g (57.6 mmol) (K8) in 800 mL anhydrous THF was cooled to −5-0° C. with ice-salts bath. 800 mL borane/THF complex was added using a stainless steel cannula during 1.5 h. The cooling bath was removed when the addition was done, let it warm up to RT during 2 h. The mixture was heated under reflux for 2 h and cooled to 15° C. 50 mL water was added dropwise to quench the excess of borane, till no hydrogen gas evolved. Solvent was evaporated and the residue was dissolved in 116N HCl, heated under reflux for 3 h and stirred at RT for 18 h. The acidic solution was basified with solid NaOH to neutral pH and extracted with 2×500 mL CHCl$_3$. Dried over Na$_2$SO$_4$. The solvent was evaporated and the residue was digested with 450 mL boiling methanol, hot filtered to remove any insoluble impurities. The filtrate sat at room temperature for 18 h. The resulting crystal was filtered and washed with 2×50 mL methanol, dried at room temperature for 24 h. to give 20.4 g white flaky crystal with melting point 107-110° C. $H^1$NMR (300 MHz, CDCl$_3$) δ (ppm) 2.20 (s, 6H, Ar—CH$_3$), 3.30 (t, 4H, NCH$_2$), 3.45 (s, 3H, OCH$_3$), 3.70-4.10 (m, 20H, OCH$_2$), 4.25 (s, 2H, ArNH), 6.50-7.10 (m, 10H, Ar—H). Anal. Calcd for C$_{33}$H$_{45}$N$_3$O$_6$: C, 68.37; H, 7.82; N, 7.25. Found: C, 67.99; H, 8.08; N, 7.24.

Example 9

Synthesis of K10. 20.4 g (35.2 mmol) K9 and 6.13 g (77.5 mmol) pyridine were dissolved in 100 mL anhydrous CH$_2$Cl$_2$ in a 125 mL additional funnel, while 8.32 g (38.7 mmol) C5 was dissolved in 125 mL CH$_2$Cl$_2$ in another 125 mL additional funnel. The solutions in two additional funnels were added slowly into a 2 l flask containing 800 mL anhydrous CH$_2$Cl$_2$ during 5 h. The resulting solution was stirred at room temperature for 20 h and then washed with 2×800 mL 0.2 N HCl, 800 mL sat. NaCl, dried over Na$_2$SO$_4$. The solvent was evaporated and the residue was purified with 80 g silica gel 60 with CHCl$_3$ and CHCl$_3$/MeOH (97/3, v/v), afforded 13.2 g (51%) white foam. $H^1$NMR (300 MHz, CDCl$_3$) δ (ppm) 2.25 (d, 6H, Ar—CH$_3$), 3.45 (s, 3H, OCH$_3$), 3.60-4.15 (m, 32H, OCH$_2$ and NCH$_2$), 6.50-7.00 (m, 10H, Ar—H). Anal. Calcd for C$_{39}$H$_{51}$N$_3$O$_{10}$: C, 64.89; H, 7.12; N, 5.82. Found: C, 62.57; H, 7.13; N, 5.53.

Example 10

Synthesis of K11. 13.1 g (18.3 mmol) K10 was dissolved in 250 mL anhydrous THF, cooled to −5-0° C. with ice-salts bath. 220 mL borane/THF complex was added using a stainless steel cannula during 40 min. The cooling bath was removed when the addition was done, let it warm up to RT during 2 h. The mixture was heated under reflux for 2 h and cooled to 15° C. 10 mL water was added very slowly to quench the excess of borane, till no hydrogen gas evolved. Solvent was evaporated and the residue was dissolved in 200 mL 6N HCl, heated under reflux for 3 h and stirred at RT for 18 h. The acidic solution was basified with solid LiOH to neutral pH, and extracted with 2×300 mL CHCl$_3$. Dried over Na$_2$SO$_4$. The solvent was evaporated and the residue was purified with 30 g silica gel 60 with CHCl$_3$ as eluent, afforded 8.0 g oil, which crystallized upon cooling. $H^1$NMR (300 MHz, CDCl$_3$) δ (ppm) 2.20 (s, 6H, Ar—CH$_3$), 3.30-4.20 (m, 39H, OCH$_3$, OCH$_2$ and NCH$_2$), 6.50-7.10 (m, 10H, Ar—H). Anal. Calcd for C$_{39}$H$_{55}$N$_3$O$_8$: C, 67.51; H, 7.99; N, 6.06. Found: C, 67.29; H, 8.08; N, 6.00.

Example 11

Synthesis of K12 (4-Nitro, R═H). K11 (0.69 g, 1 mmol) was dissolved in 10 mL tetrahydrofuran and the resulting solution was diluted with 10 mL methanol. To this solution 0.36 g (1.5 mmol) 4-nitrophenyldiazonium tetrafluoroborate was added. The suspension was stirred at room temperature for 2 hours. TLC showed that there was still un-reacted K11 left. 0.36 g (1.5 mmol) more 4-nitrophenyldiazonium tetrafluoroborate was added and continued to stir for another 2 hours. When TLC showed that K11 was gone, the solvent was evaporated and the residue was dissolved in 100 mL chloroform, washed 100 mL water. The solvent was evaporated to get about 1.0 g oily gum. This crude product was purified with a short column, packed with 7.5 g silica gel, eluted with chloroform to remove front impurities, then using chloroform/methanol (97/3, v/v) to get 0.32 g dark red gum.product. $H^1$NMR (300 MHz, CDCl$_3$) δ (ppm) 2.30 (s, 6H, Ar—CH$_3$), 3.40-4.50 (m, 39H, OCH$_3$, OCH$_2$ and NCH$_2$), 6.70-7.70 (m, 9H, Ar—H) 7.82 (d, 2H, H—Ar—NO$_2$), 8.20 (d, 2H, H—Ar—NO$_2$).

Example 12

Synthesis of K12 (R═COOEt)

General Procedure for Synthesis of Ethylbenzoates: The solution of appropriate acid 10 g (54.9 mmol for I-III) and concentrated sulfuric acid 10.76 g (105 mmol) in 200 mL ethanol was refluxed overnight (about 18 hours). Most of ethanol was evaporated, resulted residue was dissolved in 200 mL CHCl$_3$, washed with 500 mL 2.5% Na$_2$CO$_3$ and 500 DI water and then dried over anhydrous sodium sulfate. The solution was filtered and solvent was evaporated to afford yellow solid, not further purification was directly used into next reaction.

For 4-amino-3-nitro-ethylbenzoate: yield 95%, $^1$H-NMR (300 MHz, CDCl$_3$) δ 8.8 (d, 1H), 8.0 (dd, 1H), 7.8 (d, 1H), 6.4 (w, 2H), 4.4 (q, 2H), 1.4 (t, 3H).

For 2-amino-4-nitro-ethylbenzoate: yield 90%, $^1$H-NMR (300 MHz, CDCl$_3$) δ 8.8 (d, 1H), 8.1 (dd, 1H), 6.6 (d, 1H), 4.4 (q, 2H), 1.4 (t, 3H).

Under the cooling of ice-water bath, sodium nitride 0.103 g (1.5 mmol) was added to 2.4 g (25 mmol) concentrated sulfuric acid and stood for five minutes, then warmed to 60° C., the solution became clear. The solution was cooled to under 0° C. with ice-salt bath; the appropriate amino-ethyl-benzoate 0.315 mg (1.5 mmol) was added in one portion. The solution was kept at under 0° C. and stirred for two hours. KI-starch paper monitored the free nitrous acid until reaction completed. Under the cooling of ice-water, the solution was slowly transferred into the solution of K11 1.04 g (1.5 mmol) and sodium acetate 6.84 g (50 mmol) in 50 mL acetic acid. The solution became immediately red. The mixture was stirred overnight and warmed to room temperature. The mixture was poured into stirring 400 mL DI water, extracted with 200 mL chloroform. The organic layer washed with 200 mL sat. sodium carbonate, 200 mL DI water, dried over anhydrous sodium sulfate. The solvent was evaporated and the residue was further purified with 10 g silica gel 60 using chloroform:cyclohexane 1:1 (v/v) as elution to remove impurity and chloroform to afford dark red product, which was dissolved in 10 mL methanol.

5 mmol sodium hydride was then added, the resulted solution was stirred overnight at room temperature to afford following:

For 2-Carboxy-4-nitro-K12: yield 92%, $^1$H-NMR (300 MHz, CDCl$_3$) δ 6.5-8.9 (m, 12H), 3.2-4.5 (m, 41H), 2.2 (d, 6H), 1.4 (m, 3H).

For 4-Carboxy-2-nitro-K12: yield 85%, $^1$H-NMR (300 MHz, CDCl$_3$) δ 6.7-8.1 (m, 12H), 3.3-4.5 (m, 41H), 2.2 (d, 6H), 1.4 (t, 3H).

For 3-Carboxy-4-nitro-K12: yield 95%, $^1$H-NMR (300 MHz, CDCl$_3$) δ 6.8-8.1 (m, 12H), 3.3-4.5 (m, 41H), 2.3 (m, 6H), 1.4 (t, 3H).

K13 (R=H) was obtained by same procedure. Yield 89%, $^1$H-NMR (300 MHz, CDCl$_3$) δ 6.5-7.7 (m, 11H), 3.2-4.4 (M, 43H), 2.2 (d, 6H), 1.3 (t, 3H).

K13 (R=CH$_2$COOH) was obtained by same procedure. Yield 54%, $^1$H-NMR (300 MHz, CDCl$_3$) δ 6.7-7.7 (m, 10H), 3.2-4.4 (M, 45H), 2.2 (d, 6H).

K13 (R=NO$_2$) was obtained by same procedure. Yield 67%, $^1$H-NMR (300 MHz, CDCl$_3$) δ 6.7-7.9 (m, 10H), 3.2-4.4 (M, 43H), 2.2 (d, 6H).

Example 13

Synthesis of K14. A solution of 8.50 g (12.3 mmol) K11 in 46 mL DMF, was cooled to −5-0° C. 18.9 g (123 mmol) POCl$_3$ was added during 1 h, while the temperature was kept below 0° C. The ice bath was removed when the addition was complete. The solution was stirred at room temperature for 18 h, then warmed to 70° for 1 h, and poured into 420 mL icy water, basified with solid Na$_2$CO$_3$ to pH 7. Extracted with 400 mL CHCl$_3$, dried over Na$_2$SO$_4$, Solvent was evaporated, afforded 9.08 g (102%) light yellow oil. This oil may still contain about 10% DMF, and was used directly for next step reaction with further purification. H$^1$NMR (300 MHz, CDCl$_3$) δ (ppm) 2.20 (s, 6H, Ar—CH$_3$), 3.30-4.20 (m, 39H, OCH$_3$, OCH$_2$ and NCH$_2$), 6.50-7.10 (m, 9H, Ar—H), 9.75 (s, 1H, ArCHO). Anal. Calcd for C$_{39}$H$_{55}$N$_3$O$_8$+HCON(CH$_3$)$_2$: C, 64.97; H, 7.86; N, 7.05. Found: C, 62.59; H, 7.83; N, 6.57.

Example 14

Synthesis of K15. K14 (0.72 g, 1 mmol) was dissolved in 10 mL tetrahydrofuran and the resulting solution was diluted with 50 mL ethanol. To this solution 0.81 g (2.5 mmol) 2-methyl-1-(3-sulfopropyl)naphtho[1,2-d]thiazolium inner salts and 0.10 g triethylamine were added. The resulting solution was stirred under reflux for 18 h. after cooling. The solvent was evaporated and the residue was purified by a silica gel column with CHCl$_3$/methanol as eluent to give 0.48 g dark brown powder. $^1$H-NMR (300 MHz, CDCl$_3$) δ 6.8-8.1 (m, 17H), 3.3-4.5 (m, 45H), 2.3 (s, 6H), 2.1 (m, 2H).

Method of Determining Potassium Ions

Figure 2:
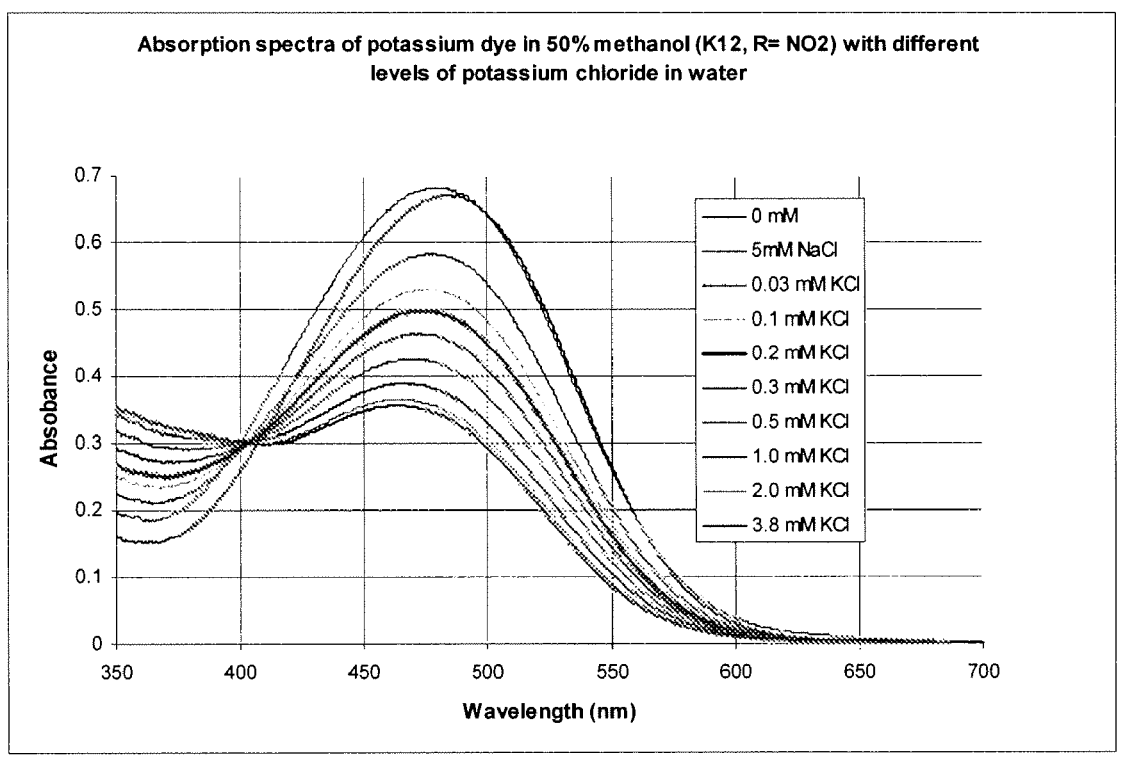
FIG. 2 is a graph illustrating the absorbance of a potassium colorimetric indicator in accordance with the invention versus potassium concentration aqueous sample.

Solvents and reagents are purchased from Aldrich (Milwaukee, Wis.) and used without further purification. Analytical grade buffer and inorganic salts are purchased from either Fluka AG (Buchs, Switzerland) or Sigma Co. (St. Louis, Mo.). Absorption measurements are performed with a Shimadzu UV2101PC spectrophotometer equipped with a jacketed cuvette holder for controlling of temperature. Titration of a chromoinophore is carried out in the following manner: A methanolic solution of a chromoionophore is diluted with buffer, deionized water or deionized water with organic co-solvent in a volumetric flask to make about 30 μM final solution, the required amount of solid salt is added and the solution's absorption spectrum is measured. The typical titration spectra are shown in FIG. 2.

Figure 3:
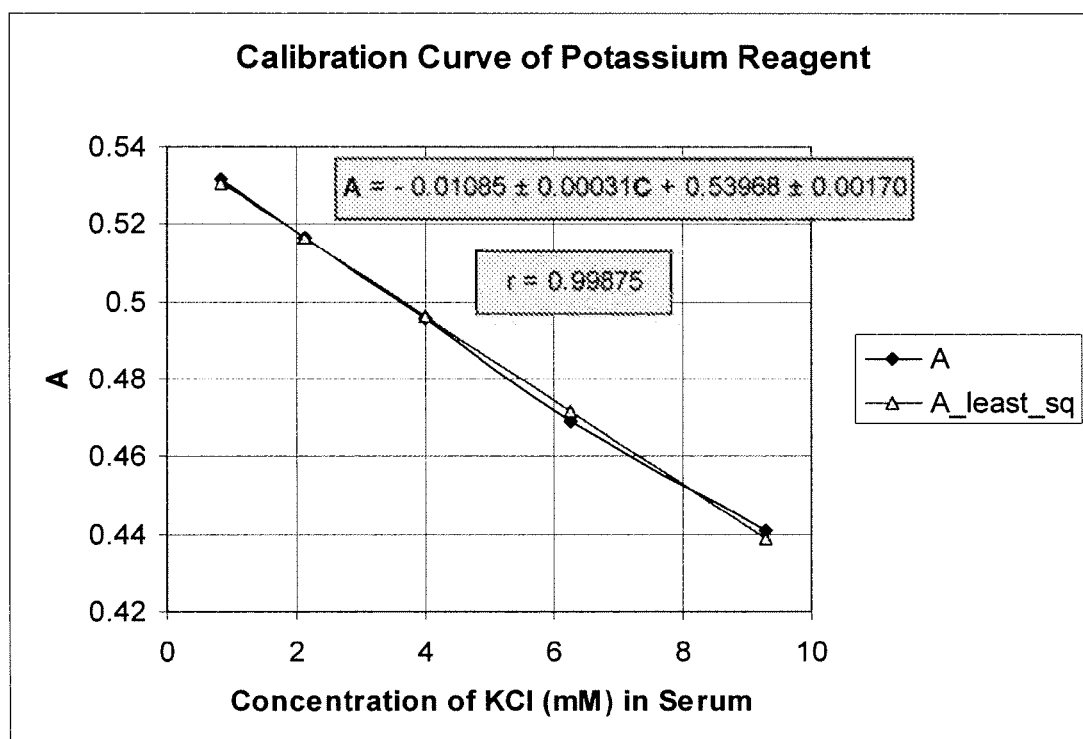
FIG. 3 is a graph illustrating a calibration curve a potassium colorimetric indicator in accordance with the invention versus potassium concentration aqueous sample.

Potassium colorimetric reagent used for FIG. 3 is formulated as follows: a methanolic solution containing of about 4.5 mg of colorimetric potassium indicator K12 (4-Nitro, R=H) is mixed with 0.163 g 2-methoxyphenylaza-15-crown-5, 2.0 g tetrabutylammonium hydroxide and 0.0292 g ethylenediaminetetraacetic acid. The resulting mixture is dissolved in 1/1 (v/v) of methanol/isopropanol and the total volume is brought to 100 ml. 2.7 ml of this solution is mixed with 0.3 ml serum or aqueous sample, and incubated at 37° C. for 5 min. The absorption values are recorded at wavelength of 486 nm, and are used to plot the chart shown in FIG. 3.

What is claimed is:

1. A chromoionophore of the general Formula (I)

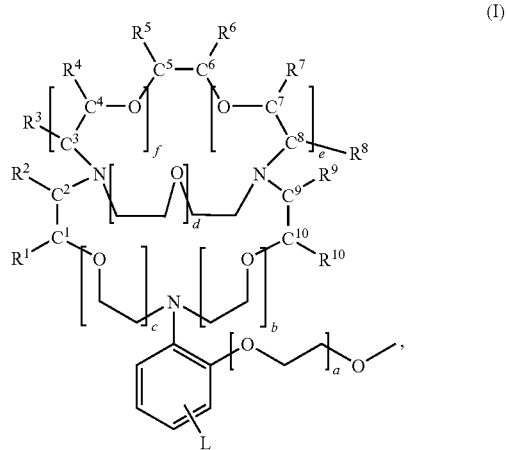

wherein
a is 0 or 1,
b and c independently are selected from the group consisting of 0 and 1, with the proviso that b and c are not simultaneously 0,
d is selected from the group consisting of 1, 2 and 3,
e and f independently are selected from the group consisting of 0 and 1, with the proviso that e and f are not simultaneously 0,
each of $R^1$ and $R^2$ is hydrogen or $R^1$ and $R^2$, together with $C^1$ and $C^2$, combine to form a ($C_1$-$C_4$) alkyl benzene ring or a ($C_1$-$C_4$) alkoxy benzene ring;
each of $R^3$ and $R^4$ is hydrogen or $R^3$ and $R^4$, together with $C^3$ and $C^4$, form a ($C_1$-$C_4$) alkyl benzene ring or a ($C_1$-$C_4$) alkoxy benzene ring;
each of $R^5$ and $R^6$ is hydrogen or $R^5$ and $R^6$, together with $C^5$ and $C^6$, form a benzene ring or a naphthalene ring;
each of $R^7$ and $R^8$ is hydrogen or $R^7$ and $R^8$, together with $C^7$ and $C^8$, form a ($C_1$-$C_4$) alkyl benzene ring or a ($C_1$-$C_4$) alkoxy benzene ring;
each of $R^9$ and $R^{10}$, is hydrogen or $R^9$ and $R^{10}$, together with $C^9$ and $C^{10}$, form a ($C_1$-$C_4$) alkyl benzene ring or a ($C_1$-$C_4$) alkoxy benzene ring; and
L is a chromophoric moiety selected from the group consisting of —$NO_2$, Formula (II) and (III),

wherein
Ar is a ($C_6$-$C_{10}$) aromatic moiety or a ($C_5$-$C_{14}$) heteroaromatic moiety containing one or more heteroatoms selected from N, O, and S, and wherein Ar is substituted with one or more substituents selected from the group consisting of hydrogen, —$NO_2$, —NO, —CN, ($C_1$-$C_8$) straight chain or branched alkyl, ($C_2$-$C_8$) alkenyl, halogen, —$SO_3H$, —W—COOH, —W—N($R^{11}$)$_3$, —C(O)$OR^{11}$, —C(O)$R^{11}$;
W is ($C_1$-$C_8$) alkylene; and
$R^{11}$ is selected from the group consisting of hydrogen and ($C_1$-$C_8$) straight chain or branched alkyl.

2. The chromoionophore according to claim 1, wherein Ar is selected from the group consisting of Formula (IV), (V), (VI), and (VII)

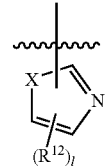

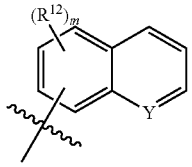

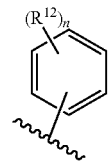

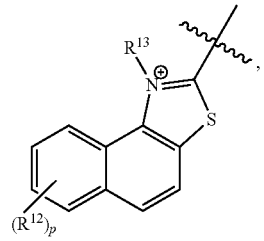

wherein
X is O or S;
Y is N or C;
$R^{12}$, at each occurrence, is independently selected from the group consisting of hydrogen, —$NO_2$, —NO, —CN, $C_1$-$C_8$ straight chain or branched alkyl, ($C_2$-$C_8$) alkenyl, halogen, —$SO_3H$, -Q-COOH, -Q-N($R^{14}$)$_3$, —C(O)$OR^{14}$, —C(O)$R^{14}$;
$R^{13}$ is -Q-$SO_3^-$ or -Q-$COO^-$;
Q is ($C_1$-$C_8$) alkylene;
$R^{14}$ is selected from the group consisting of hydrogen and ($C_1$-$C_8$) straight chain or branched alkyl;
l is an integer selected from 1 to 3;
m is an integer selected from 1 to 7;
n is an integer selected from 1 to 5; and
p is an integer selected from 1 to 6.

3. The chromoionophore according to claim 1, wherein
a=1, b=1, c=1, d=1, e=1, f=1;
each of $R^3$, $R^4$, $R^5$, $R^6$, $R^7$, and $R^8$ is hydrogen;
$R^1$ and $R^2$, together with $C^1$ and $C^2$, form a toluene ring;
$R^9$ and $R^{10}$, together with $C^9$ and $C^{10}$, form a toluene ring.

4. The chromoionophore according to claim 1, wherein
a=1, b=1, c=1, d=2, e=1, f=1;
each of $R^3$, $R^4$, $R^5$, $R^6$, $R^7$, and $R^8$ is hydrogen;
$R^1$ and $R^2$, together with $C^1$ and $C^2$, form a toluene ring;
$R^9$ and $R^{10}$, together with $C^9$ and $C^{10}$, form a toluene ring.

5. The chromoionophore according to claim 1, wherein
a=0, b=1, c=1, d=2, e=1, f=1;
each of $R^3$, $R^4$, $R^5$, $R^6$, $R^7$, and $R^8$ is hydrogen;
$R^1$ and $R^2$, together with $C^1$ and $C^2$, form a toluene ring;
$R^9$ and $R^{10}$, together with $C^9$ and $C^{10}$, form a toluene ring.

6. The chromoionophore according to claim 1, wherein the chromoionophore is selected from the group consisting of
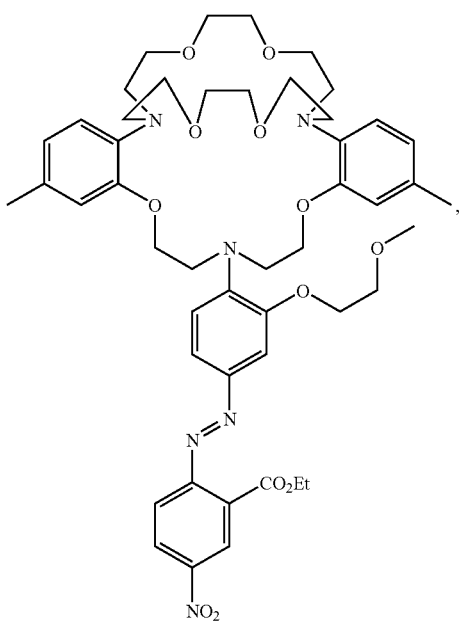
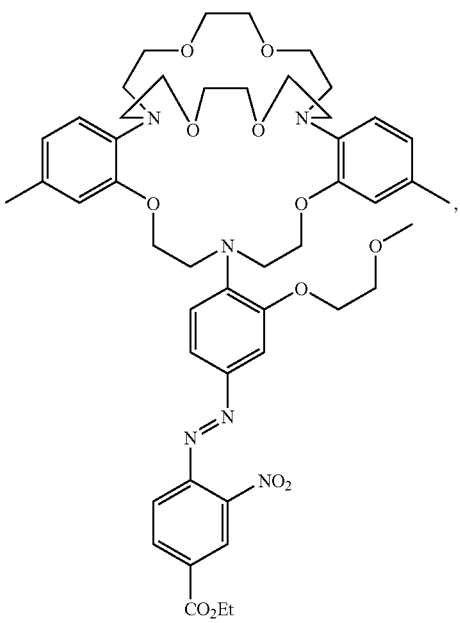
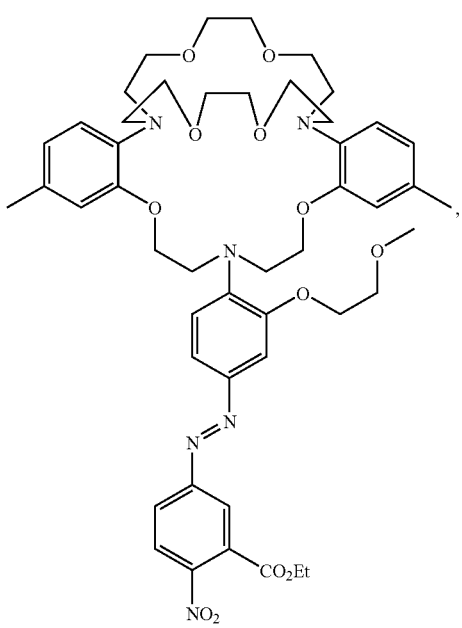
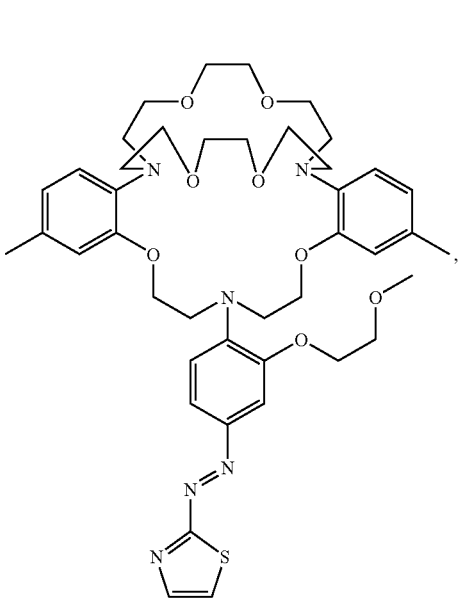

23

-continued

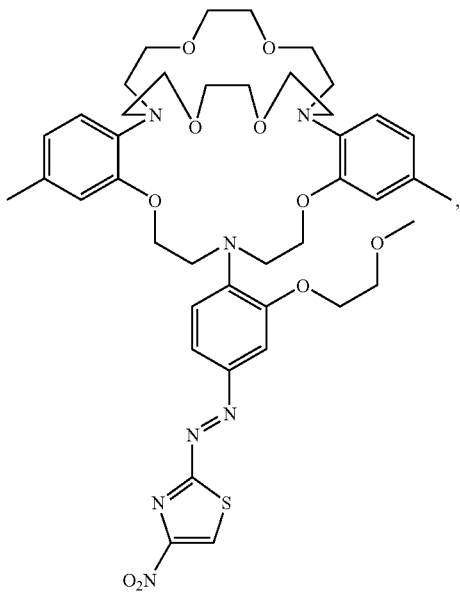

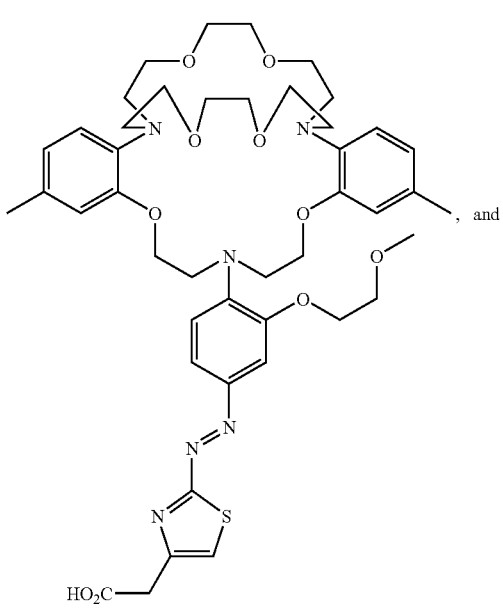
, and

24

-continued

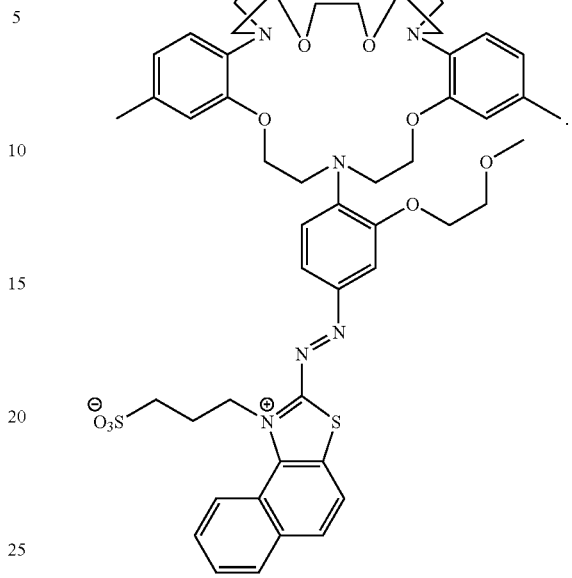

7. A method of determining the concentration of potassium ions in a sample comprising
(a) measuring the intensity of at least one absorption maximum of a solution of a chromoionophore sensitive to the presence of potassium ions in solution to obtain a first intensity; wherein the concentration of the chromoionophore in solution is known; and
wherein said at least one absorption maximum has a wavelength in the visible region; and
wherein the chromoionophore is of the general Formula (I)

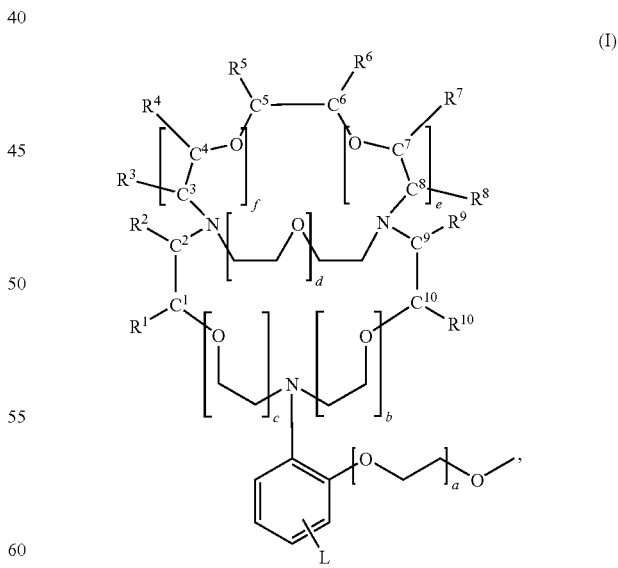

(I)

wherein
a is 0 or 1,
b and c independently are selected from the group consisting of 0 and 1, with the proviso that b and c are not simultaneously 0, d is selected from the group consisting of 1, 2 and 3, e and f independently are selected from the group consisting of 0 and 1, with the proviso that e and f are not simultaneously 0, each of $R^1$ and $R^2$ is hydrogen or $R^1$ and $R^2$, together with $C^1$ and $C^2$, combine to form a ($C_1$-$C_4$) alkyl benzene ring or a ($C_1$-$C_4$) alkoxy benzene ring;

each of $R^3$ and $R^4$ is hydrogen or $R^3$ and $R^4$, together with $C^3$ and $C^4$, form a ($C_1$-$C_4$) alkyl benzene ring or a ($C_1$-$C_4$) alkoxy benzene ring;

each of $R^5$ and $R^6$ is hydrogen or $R^5$ and $R^6$, together with $C^5$ and $C^6$, form a benzene ring or a naphthalene ring;

each of $R^7$ and $R^8$ is hydrogen or $R^7$ and $R^8$, together with $C^7$ and $C^8$, form a ($C_1$-$C_4$) alkyl benzene ring or a ($C_1$-$C_4$) alkoxy benzene ring;

each of $R^9$ and $R^{10}$ is hydrogen or $R^9$ and $R^{10}$, together with $C^9$ and $C^{10}$, form a ($C_1$-$C_4$) alkyl benzene ring or a ($C_1$-$C_4$) alkoxy benzene ring; and L is a chromophoric moiety selected from the group consisting of —$NO_2$, Formula (II) and (III),

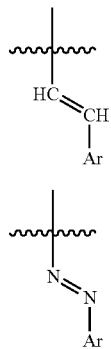

wherein

Ar is a ($C_6$-$C_{10}$) aromatic moiety or a ($C_5$-$C_{14}$) heteroaromatic moiety containing one or more heteroatoms selected from N, O, and S, and wherein Ar is substituted with one or more substituents selected from the group consisting of hydrogen —$NO_2$, —NO, —CN, ($C_1$-$C_8$) straight chain or branched alkyl, ($C_2$-$C_8$) alkenyl, halogen, —$SO_3H$, —W—COOH, —W—N($R^{11}$)$_3$, —C(O)O$R^{11}$, —C(O)$R^{11}$;

W is ($C_1$-$C_8$) alkylene; and $R^{11}$ is selected from the group consisting of hydrogen and ($C_1$-$C_8$) straight chain or branched alkyl (b) contacting the solution of the chromoionophore with the sample; whereby the first intensity changes;

(c) measuring the intensity of at least one absorption maximum to obtain a second intensity;

(d) deriving the concentration of potassium ion in the sample based, in part, on the difference between the first and second intensities.

8. The method according to claim 7, wherein the absorption maximum occurs at a wavelength of about 400 nm or greater.

9. The method according to claim 7, wherein absorption maximum occurs at a wavelength between about 400 nm and about 800 nm.

10. The method according to claim 7, wherein Ar is selected from the group consisting of Formula (IV), (V), (VI), and (VII)

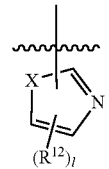

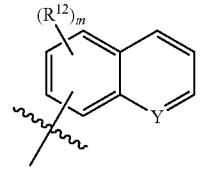

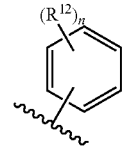

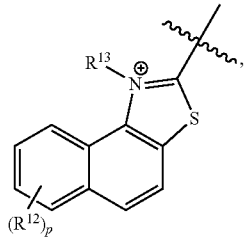

wherein

X is O or S;

Y is N or C;

$R^{12}$, at each occurrence, is independently selected from the group consisting of hydrogen, —$NO_2$, —NO, —CN, $C_1$-$C_8$ straight chain or branched alkyl, ($C_2$-$C_8$) alkenyl, halogen, —$SO_3H$, -Q-COON, -Q-N($R^{14}$)$_3$, —C(O)O$R^{14}$, —C(O)$R^{14}$;

$R^{13}$ is -Q-$SO_3^-$ or -Q-COO$^-$;

Q is ($C_1$-$C_8$) alkylene;

$R^{14}$ is selected from the group consisting of hydrogen and ($C_1$-$C_8$) straight chain or branched alkyl;

l is an integer selected from 1 to 3;

m is an integer selected from 1 to 7;

n is an integer selected from 1 to 5; and p is an integer selected from 1 to 6.

11. The method according to claim 7, wherein the chromoionophore has a=1, b=1, c=1, d=1, e=1, f=1;

each of $R^3$, $R^4$, $R^5$, $R^6$, $R^7$, and $R^8$ is hydrogen;

$R^1$ and $R^2$, together with $C^1$ and $C^2$, form a toluene ring;

$R^9$ and $R^{10}$, together with $C^9$ and $C^{10}$, form a toluene ring.

12. The method according to claim 7, wherein the chromoionophore has a=1, b=1, c=1, d=2, e=1, f=1;

each of $R^3$, $R^4$, $R^5$, $R^6$, $R^7$, and $R^8$ is hydrogen;

$R^1$ and $R^2$, together with $C^1$ and $C^2$, form a toluene ring;

$R^9$ and $R^{10}$, together with $C^9$ and $C^{10}$, form a toluene ring.

13. The method according to claim 7, wherein the chromoionophore has a=0, b=1, c=1, d=2, e=1, f=1;

each of $R^3$, $R^4$, $R^5$, $R^6$, $R^7$, and $R^8$ is hydrogen;

$R^1$ and $R^2$, together with $C^1$ and $C^2$, form a toluene ring;
$R^9$ and $R^{10}$, together with $C^9$ and $C^{10}$, form a toluene ring.
14. The method according to claim 7, wherein the chromoionophore is selected from the group consisting of
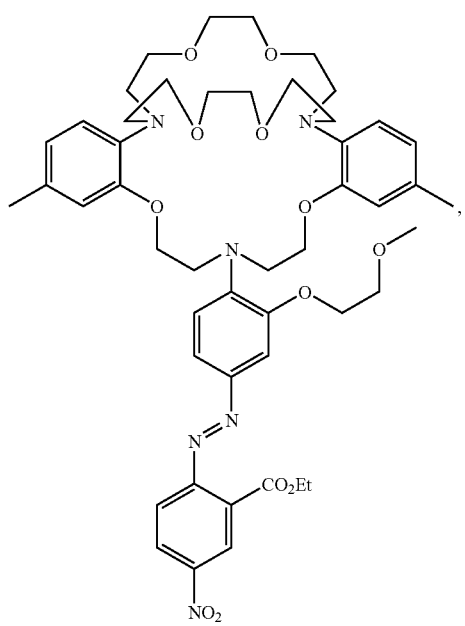
,
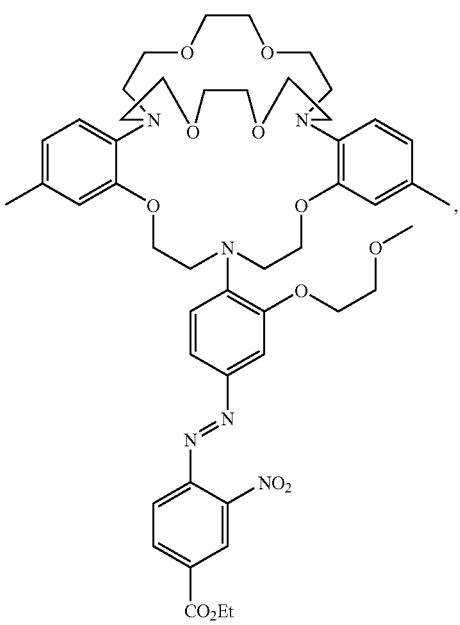
,
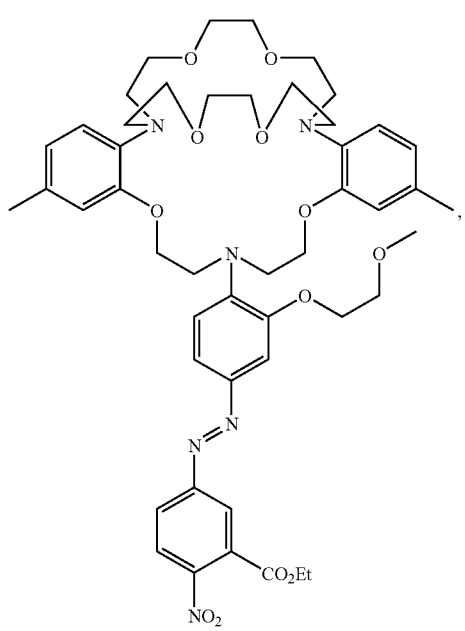
,
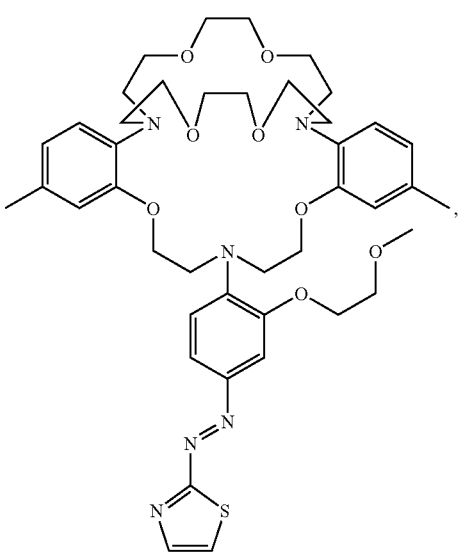
,

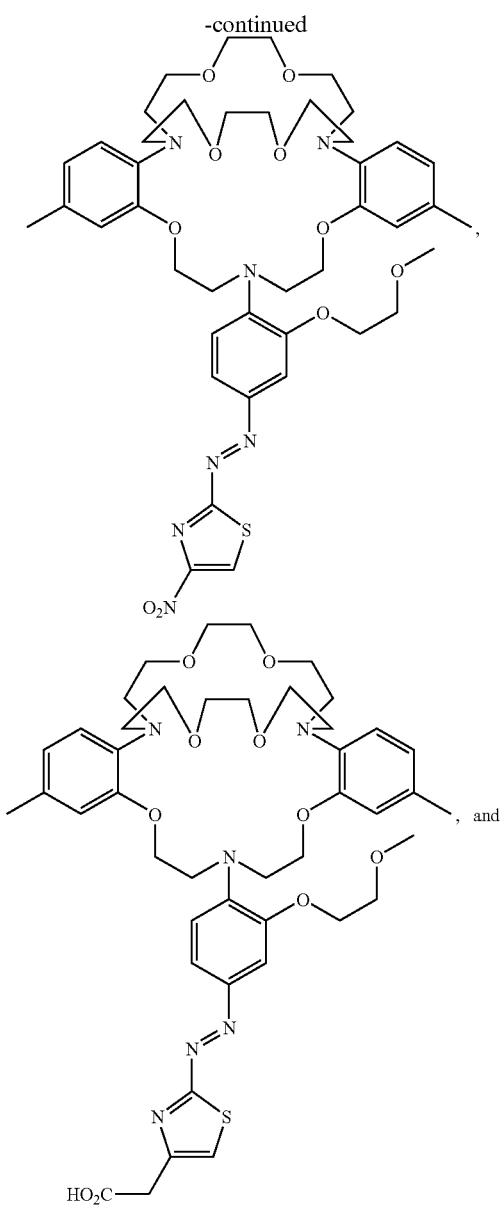
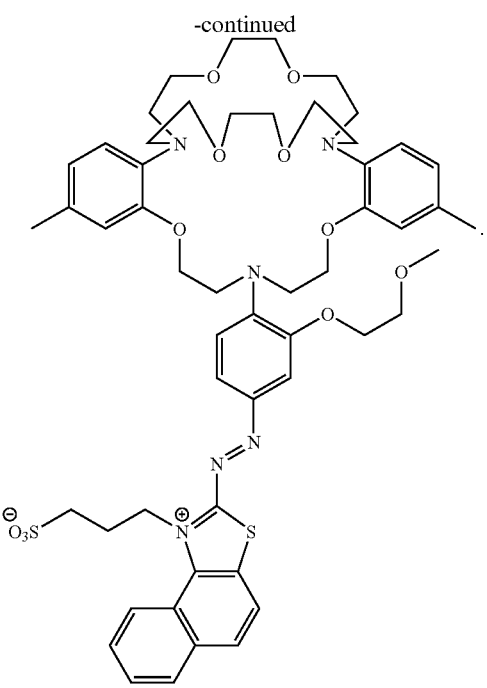
15. The method according to claim 7, wherein the sample is a biological fluid.
16. The method according to claim 15, wherein the biological fluid is selected from the group consisting of whole blood, plasma, serum, and urine.
17. The method according to claim 7, wherein the sample has a pH of 6.5 or above.
* * * * *